| United States Patent [19] | [11] 4,007,270 |
|---|---|
| Bernstein et al. | [45] Feb. 8, 1977 |

[54] COMPLEMENT INHIBITORS

[75] Inventors: Seymour Bernstein, New City; Norman Bauman, Nanuet; Milton David Heller, New City, all of N.Y.

[73] Assignee: American Cyanamid Company, Stamford, Conn.

[22] Filed: Nov. 18, 1975

[21] Appl. No.: 632,931

[52] U.S. Cl. ............................ 424/230; 424/317
[51] Int. Cl.$^2$ .................................. A61K 31/60
[58] Field of Search .......................... 424/331, 317

[56] References Cited

OTHER PUBLICATIONS

Maeda et al., Chem. Abst. vol. 73 (1970), p. 54462c.

*Primary Examiner*—Sam Rosen
*Attorney, Agent, or Firm*—Jack W. Richards

[57] ABSTRACT

Aurin tricarboxylic acid and certain of its derivatives and salts thereof useful as complement inhibitors.

11 Claims, No Drawings

COMPLEMENT INHIBITORS

BACKGROUND OF THE INVENTION

The present invention resides in the concept of aurin tricarboxylic acid, certain of its derivatives and salts thereof and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. The standard reference for nomenclature of complement is *Bull. World Health Org.*, 39, 935–938, (1968). A more detailed discussion of the complement system and its role in body processes can be found in, for example, *Scientific American*, 229, (No. 5), 54–66 (1973); *Medical World News*, Oct. 11, 1974, pp. 53–58; 64–66; *Harvey Lectures*, 66, 75–104 (1972); *The New England Journal of Medicine*, 287, 489–495, 545–549, 592–596, 642–646 (1972); *The Johns Hopkins Med. J.*, 128, 57–74 (1971); and *Federation Proceedings*, 32, 134–137 (1973).

The complement system can be considered to consist of three subsystems: (1) a recognition unit (C1q) which enables it to combine with antibody molecules that have detected a foreign invader; (2) an activation unit, (C1r, C1s, C2, C4, C3) which prepares a site on the neighboring membrane; and (3) an attack unit (C6, C7, C8, C9) which creates a "hole" in the membrane. The membrane attack unit is non-specific; it destroys invaders only because it is generated in their neighborhood in order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review of Biochemistry*, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)]benzenesulfonic acid tetrasodium salt (chlorazol fast pink), heparin and a sulphated dextran have been reported to have an anticomplementary effect, *British Journal of Experimental Pathlogy*, 33, 327–339 (1952). The compound 8,8'-[ureylenebis[m-phenylenecarboxylimino(4-methyl-m-phenylene]carboxylimino)]di-1,3,5-naphthalenetrisulfonic acid, hexasodium salt (Suramin Sodium) is described as a competitive inhibitor of the complement system, *Clin. Exp. Immunol.*, 10, 127–138 (1972). German Pat. No. 2,254,893 or South African Pat. No. 727,923 discloses certain 1-(diphenylmethyl)-4-(3-phenylallyl) piperazines useful as complement inhibitors. Other chemical compounds having complement inhibiting activity are disclosed in, for example, *Journal of Medicinal Chemistry*, 12, 415–419, 902–905, 1049–1052, 1053–1056 (1969); *Canadian Journal of Biochemistry*, 47, 547–552 (1969); *The Journal of Immunology*, 93, 629–640 (1964); *The Journal of Immunology*, 104, 279–288 (1970); *The Journal of Immunology*, 106, 241–245 (1971); and *The Journal of Immunology*, 111, 1061–1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812, (1972); *Allergol, Et. Immunopath*, II, 163–168 (1974); and *J. Allergy Clin. Immunol.*, 53, No. 5, 298–302 (1974).

SUMMARY OF THE INVENTION

It has now been discovered that certain aurins interact with the complement reaction sequence, thereby inhibiting complement activity in body fluids.

This invention is particularly concerned with aurin tricarboxylic acid, all pharmaceutically acceptable aurin tricarboxylic acid derivatives and salts of both the acid and derivatives thereof having complement inhibiting activity. Representative aurins within the scope of the present invention, include aurin tricarboxylic acid; ammonium salt of aurin tricarboxylic acid; sodium salt of aurin tricarboxylic acid; potassium salt of aurin tricarboxylic acid; methyl ester of aurin tricarboxylic acid; ethyl ester of aurin tricarboxylic acid; pentyl ester of aurin tricarboxylic acid; acetate of aurin tricarboxylic acid; propionate of aurin tricarboxylic acid and sodium salt of acetylated aurin tricarboxylic acid. Operable pharmaceutically acceptable salts of aurin tricarboxylic acid and certain of its derivatives encompassed within this invention include alkali metal salts, alkaline earth metal salts, ammonium and substituted ammonias, e.g., diethanolamine, ethylenediamine, glucamine trialylammonium (e.g., $C_1$–$C_6$ alkyl), pyridinium, etc. The preferred derivatives of this invention are the ($C_1$–$C_5$) acylates and ($C_1$–$C_5$) alkyl esters of aurin tricarboxylic acid. The preferred salts are the ammonium and alkali metal salts of both aurin tricarboxylic acid and the acylated derivatives thereof.

Aurins (free acid and ammonium salt) of this invention may be prepared according to the method of G. B. Heisig and W. M. Lauer, *Org. Syn. Coll.* Vol. 1 (second Ed.), 54–55 (1932); Holaday, D. A., *J. Am. Chem. Soc.*, 62, 989 (1940); *The Merck Index*, 8th Ed. (1968), page 42; and Caro, *Ber.*, 25, 939 (1892). Esterification with an alcohol and acylation in the presence of an acid provide the derivatives of this invention. The salts of the free acid and acylates may be obtained by treatment thereof with a suitable base in an aqueous alcohol.

This invention is concerned with a method of inhibiting the complement system in a body fluid, such as blood serum, which comprises subjecting body fluid complement to the action of an effective complement inhibiting amount of aurin tricarboxylic acid, certain of its derivatives and salts thereof. The method of use of this invention is also concerned with a method of inhibiting the complement system in a warm-blooded animal which comprises internally administering to said animal an effective complement inhibiting amount of aurin tricarboxylic acid, certain of its derivatives and salts thereof. Body fluid can include blood, plasma, serum, synovial fluid, cerebrospinal fluid, or pathological accumulations of fluid such as pleural effusion, etc.

The aurin tricarboxylic acid and certain of its derivatives and salts thereof of the present invention find utility as complement inhibitors in body fluids and as such may be used to ameliorate or prevent those pathological requiring the function of complement and in the therapeutic treatment of warm-blooded animals having immunologic diseases such as rhematoid arthritis, systemic lupus erythematosus, certain kinds of glomerulonephritis, certain kinds of autoallergic hemolytic anemia, certain kinds of platelet disorders and certain kinds of vasculitis. Aurin tricarboxylic acid, its derivatives and salts herein also be used in the therapeutic treatment of warm-blooded animals having non-immunologic diseases such as paroxysmal nocturnal hemoglobinuria, hereditary angioneurotic edema (such as Suramin Sodium, etc.) and inflammatory states induced by the action of bacterial or lysosomal enzymes on the appropriate complement components as for example, inflammation following coronary occlusion. They may be useful in the treatment of transplant rejection.

DETAILED DESCRIPTION OF THE INVENTION

The following examples describe in detail the preparation and formulation of representative compounds of the present invention.

EXAMPLE 1

Methyl ester of aurin tricarboxylic acid

A mixture of 5 g of aurin tricarboxylic acid, 100 ml of methyl alcohol and 4.5 ml of concentrated sulfuric acid is refluxed for 17 hours, then is cooled. Ethyl acetate is added, and the organic solution is washed twice with water, then several times with an aqueous saturated sodium bicarbonate solution. The organic layer is then dried over anhydrous sodium sulfate and is treated with activated charcoal. The solvent is then removed and the resulting red glass is dissolved in diethyl ether and crystallized out by scratching. The solid is then recrystallized from dimethyl ketone and diethyl ether and is dried in vacuo to give to methyl ester.

EXAMPLE 2

Acetate of aurin tricarboxylic acid

To a mixture of 5 g of aurin tricarboxylic acid in 19 ml of acetic anhydride is added 10 drops of concentrated sulfuric acid with swirling. The mixture is stirred at about 60° C for 30 minutes and is poured into an ice-water mixture. The resultant stiff oil is extracted with ethyl acetate. The organic layer is washed twice with saline solution and dried over anhydrous sodium sulfate then is treated with activated charcoal. The solvent is removed in vacuo to give a glass-like material. This material is placed on a Celite chromatographic column in heptane:methylene chloride:methyl alcohol:water, 60:40:17:14. The original cut of the column is then stripped with ethyl acetate to give 800 mg of glass. This material is then crystallized from methyl alcohol and ethyl acetate to give a small amount of amorphous solid. The residual solvent is evaporated in vacuo to give the acetate.

EXAMPLE 3

Sodium Salt of Acetate of Aurin Tricarboxylic Acid

Treatment of the acetate of aurin tricarboxylic acid with sodium carbonate in aqueous methyl alcohol gives the sodium salt.

EXAMPLE 4

Sodium Salt of Aurin Tricarboxylic Acid

Treatment of aurin tricarboxylic acid with sodium carbonate in aqueous methyl alcohol gives the sodium salt.

EXAMPLE 5

Propionate of Aurin Tricarboxylic Acid

To a mixture of 5 g of aurin tricarboxylic acid in 25 ml of propionate anhydride is added 12 drops of concentrated sulfuric acid with swirling. The mixture is stirred at about 60° C for 3 hours and is poured into an ice-water mixture. The resultant material is extracted with ethyl acetate. The organic layer is washed twice with saline solution and is dried over anhydrous sodium sulfate. The solvent is removed in vacuo to give a glass-like material which is crystallized from diethyl ester, filtered and is dried in vacuo to give the propionate.

Example 6

Preparation of Compressed Tablet

| INGREDIENT | MG/TABLET |
|---|---|
| Aurin Tricarboxylic Acid | 0.5–500 |
| Dibasic Calcium Phosphate N.F. | qs. |
| Starch USP | 40 |
| Modified Starch | 10 |
| Magnesium Stearate USP | 1–5 |

Example 7

Preparation of Compressed Tablet

| INGREDIENT | MG/TABLET |
|---|---|
| Ammonium salt of Aurin Tricarboxylic Acid | 0.5–500 |
| Dibasic Calcium Phosphate N.F. | qs. |
| Starch USP | 40 |
| Modified Starch | 10 |
| Magnesium Stearate USP | 1–5 |

Example 8

Preparation of Compressed Tablet - Sustained Action

| INGREDIENT | MG/TABLET |
|---|---|
| Aurin Tricarboxylic Acid* | 0.5–500 as acid equivalent |
| Dibasic Calcium Phosphate N.F. | qs. |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

Example 9

Preparation of Hard Shell Capsule

| INGREDIENT | MG/CAPSULE |
|---|---|
| Aurin Tricarboxylic Acid | 0.5–500 |
| Lactose, Spray Dried | qs. |
| Magnesium Stearate | 1–10 |

Example 10

Preparation of Hard Shell Capsule

| INGREDIENT | MG/CAPSULE |
|---|---|
| Ammonium Salt of Aurin Tricarboxylic Acid | 0.5–500 |
| Lactose, Spray Dried | qs. |
| Magnesium Stearate | 1–10 |

Example 11

Preparation of Oral Liquid (Syrup)

| INGREDIENT | % W/V |
|---|---|
| Aurin Tricarboxylic Acid | 0.05–5 |
| Liquid Sucrose (70%) | 75.0 |
| Methyl Paraben USP | 0.18 |
| Propyl Paraben USP | 0.02 |
| Flavoring Agent | qs. |
| Purified Water qs ad | 100.0 |

Example 12

Preparation of Oral Liquid (Elixir)

| INGREDIENT | % W/V |
|---|---|
| Aurin Tricarboxylic Acid | 0.05–5 |
| Alcohol USP | 12.5 |
| Glycerin USP | 45.0 |
| Flavoring Agent | qs. |

Example 12-continued

Preparation of Oral Liquid (Elixir)

| INGREDIENT | % W/V |
|---|---|
| Purified Water qs ad | 100.0 |

Example 13

Preparation of Oral Suspension (Syrup)

| INGREDIENT | % W/V |
|---|---|
| Aurin Tricarboxylic Acid* | 0.05–5 (acid equivalent) |
| Polysorbate 80 USP | 0.1 |
| Magnesium Aluminum Silicate, Colloidal | 0.3 |
| Flavoring Agent | qs. |
| Methyl Paraben USP | 0.18 |
| Propyl Paraben USP | 0.02 |
| Liquid Sucrose (70%) | 75.0 |
| Purified Water qs ad | 100.0 |

*As aluminum lake, micronized

Example 14

Preparation of Injectable Solution

| INGREDIENT | % W/V |
|---|---|
| Acetylated Aurin Tricarboxylic Acid | 0.05–5 |
| Benzyl Alcohol N.F. | 0.9 |
| Water for Injection qs ad | 100.0 |

Example 15

Preparation of Injectable Oil

| INGREDIENT | % W/V |
|---|---|
| Acetylated Aurin Tricarboxylic Acid | 0.05–5 |
| Benzyl Alcohol N.F. | 1.5 |
| Sesame Oil qs ad | 100.0 |

Example 16

Preparation of Injectable Depo Suspension

| INGREDIENT | % W/V |
|---|---|
| Acetylated Aurin Tricarboxylic Acid as aluminum lake, micronized | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs. |
| Water for Injection qs ad | 100.0 |

Example 17

Preparation of Intra-Articular Preparation

| | |
|---|---|
| Acetylated aurin tricarboxylic acid (micronized) | 2–20 mg |
| Sodium Chloride (physiological saline) | 0.9% |
| Benzyl alcohol | 0.9% |
| Sodium carboxymethylcellulose (NaCMe)* | 1–5% |
| pH adjusted to 5.0–7.5 | |
| Water for injection qs to | 100% |

*Increasing the NaCMe forms a syrupy solution of water-soluble compounds. Sterile fill in individual vials under nitrogen.

Aurin tricarboxylic acid and its derivatives thereof which are the essence of this invention may be administered internally, e.g., orally or parenterally, such as intra-articularly, to a warm-blooded animal to inhibit complement in the body fluid of the animal, such inhibition being useful in the amelioration of prevention of those reactions depending upon the function of complement, such inflammatory process and cell membrane damage induced by antigen-antibody complexes. A range of doses may be employed depending on the mode of administration, the condition being treated and the particular aurin tricarboxylic acid or derivative being used. For example, for the intravenous or subcutaneous use from about 5 to about 50 mg/kg/day, or every six hours for more rapidly excreted salts, may be used. For intra-articular use for large joints, such as the knee, from about 2 to about 20 mg/joint per week may be used, with proportionally smaller doses for smaller joints. The dosage range is to be adjusted to provide optimum therapeutic response in the warm-blooded animal being treated. In general, the amount of aurin tricarboxylic acid or derivative administered can vary over a wide range to provide from about 5 mg/kg to about 100 mg/kg of body weight of animal per day. The usual daily dosage for a 70 kg subject may vary from about 350 mg to about 3.5 g. Unit doses of the salt can contain from about 0.5 to about 500 mg.

In therapeutic use the compound of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e. oral or parenteral. The compounds can be used in compositions such as tablets. Here, the principal active ingredient is mixed with conventional tableting ingredients such as corn starch, lactose, sucrose, sorbitol, talc, stearic acid, magnesium stearate, dicalcium phosphate, gums, or similar materials as non-toxic pharmaceutically aceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The pills may be colored (e.g. pink) through use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for perenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C - Shunt inhibitor) — In this test human erythrocytes rendered fragile are lysed in autologous serum via the shunt pathway by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman anti-serum. The lesion is measured in terms of diameter, edema and hemorrhage and the extent to which combined index of these is inhibited by prior intraperitoneal injection of the test compound at 200 mg/kg is then reported unless otherwise stated; (v) Forssman Shock Test — Lethal shock is produced in guinea pigs by an i.v. injection of anti-Frossman antiserum. The harmonic mean death time of treated guinea pigs is compared with that of simultaneous controls; (vi) Complement Level Reduction Test — In this test, the above dosed guinea pigs, or others are bled for serum. The complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (iv) or intraperitoneally (ip) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of in vitro tests, Code 026, 035 and 036 and the Cap 50 test and Forssman Vasculitis test. Table I shows that the compounds of the invention possess highly significant in situ and in vivo, complement inhibiting activity in warm-blooded animals.

Table I

| COMPOUND | IN VITRO ACTIVITY | | | CAP 50* mcg/ml | IN VIVO ACTIVITY GUINEA PIG | |
|---|---|---|---|---|---|---|
| | Cl 026* | C-Late 035* | Shunt Inhib- 036* | | Forssman Vasculitis | % Complement Reduction |
| Aurin tricarboxylic acid | 9, 8** | 2 | 5 | 211 | 74, 72 | 92, 88 |
| Methyl ester of aurin tricarboxylic acid | 2 | 1 | 1 4 3 | | — | — |
| Acetate of aurin tricarboxylic acid | 12 | 2 | 6 5 | | 62 | 94 |
| Propionate of aurin tricarboxylic acid | 7 | 3 | 5 | | 48 | 91 |

*Code designation for tests employed and referred to herein
**Numbers represent the number of wells showing activity in a two-fold serial dilution assay. The higher the number the higher the activity.

We claim:
1. A method of inhibiting the complement system in a warm-blooded animal in need of such therapy which comprises internally administering to said animal an effective complement inhibiting amount of pharmaceutically acceptable compound selected from the group consisting of aurin tricarboxylic acid, ($C_1$–$C_5$) acylates thereof, ($C_1$–$C_5$) alkyl esters thereof and salts thereof.
2. A method according to claim 1 wherein the derivative is the $C_1$–$C_5$ alkyl ester of aurin tricarboxylic acid.
3. A method according to claim 1 wherein the derivative is the $C_1$–$C_5$ acylate of aurin tricarboxylic acid.
4. A method according to claim 1 wherein the salt is the alkali metal salt of aurin tricarboxylic acid.
5. A method according to claim 1 wherein the salt is the alkali metal salt of the $C_1$–$C_5$ acylate of aurin tricarboxylic acid.
6. A method according to claim 1 wherein the compound is aurin tricarboxylic acid.
7. A method according to claim 1 wherein the salt is the ammonium salt of aurin tricarboxylic acid.
8. A method according to claim 1 wherein the compound is administered intra-articularly.
9. A method according to claim 2 wherein the derivative is the methyl ester of aurin tricarboxylic acid.
10. A method according to claim 3 wherein the derivative is the acetate of aurin tricarboxylic acid.
11. A method according to claim 3 wherein the derivative is the propionate of aurin tricarboxylic acid.

* * * * *